Figure 1A:
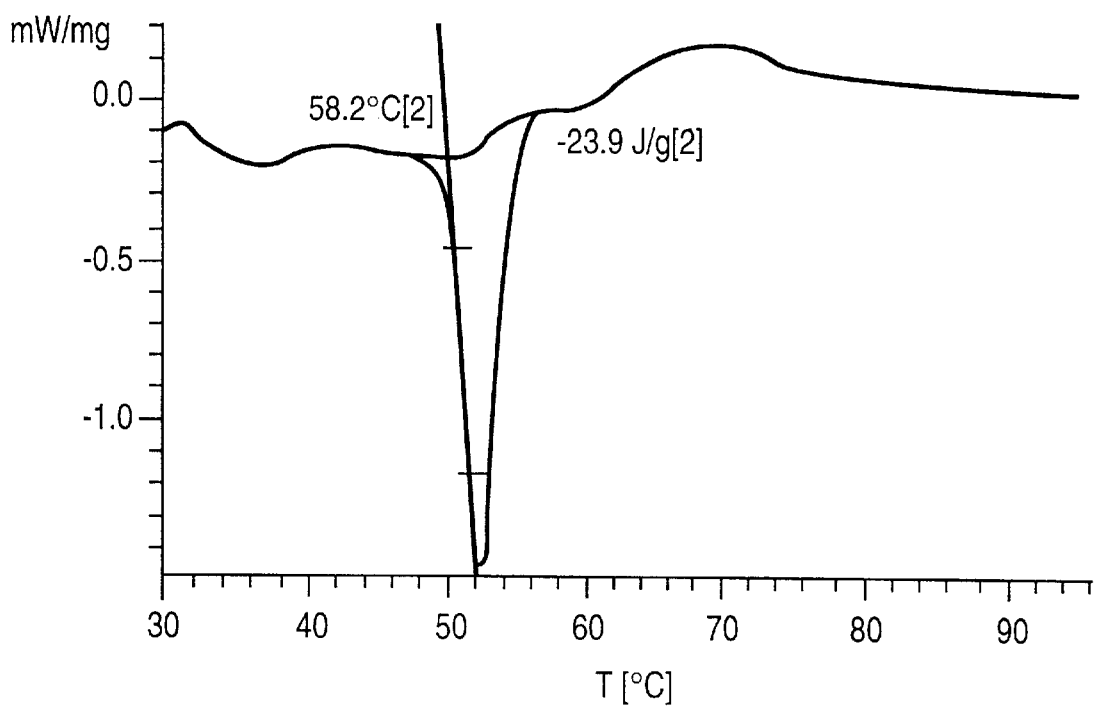

United States Patent [19]

Müller et al.

[11] Patent Number: 5,858,344
[45] Date of Patent: Jan. 12, 1999

[54] ORAL ADMINISTRATION FORM HAVING ACID ACTIVE SUBSTANCES AND A PROCESS FOR ITS PRODUCTION

[75] Inventors: Walter Müller, Neuwied; Karsten Cremer, Bonn, both of Germany

[73] Assignee: LTS Lohmann Therapie-Systeme GmbH, Neuwied, Germany

[21] Appl. No.: 693,101
[22] PCT Filed: Dec. 8, 1994
[86] PCT No.: PCT/EP94/04082
§ 371 Date: Sep. 13, 1996
§ 102(e) Date: Sep. 13, 1996
[87] PCT Pub. No.: WO95/20394
PCT Pub. Date: Aug. 3, 1995

[30] Foreign Application Priority Data

Jan. 27, 1994 [DE] Germany .......... 44 02 379.0

[51] Int. Cl.⁶ ............... A61K 31/735; A61K 31/765; A61K 31/19
[52] U.S. Cl. .......... 424/78.1
[58] Field of Search ............ 424/78.15, 78.1, 424/78.12

[56] References Cited

U.S. PATENT DOCUMENTS 4,996,047   2/1991   Kelleher et al. .......... 424/78.15

Primary Examiner—Peter F. Kulkosky
Attorney, Agent, or Firm—Wenderoth, Lind & Ponack, L.L.P.

[57] ABSTRACT

An oral administration form with a carrier for acid active substances wherein the active substance has at least one free carboxyl group ionically bound to a polymer having tertiary amino groups is characterized by the fact that the polymer is colestipol or colestipol hydrochloride.

13 Claims, 3 Drawing Sheets

ORAL ADMINISTRATION FORM HAVING ACID ACTIVE SUBSTANCES AND A PROCESS FOR ITS PRODUCTION

The present invention relates to an oral administration form with an active substance carrier wherein the active substance has at least one free carboxyl group ionically bound to a polymer having tertiary amino groups. The present invention further relates to a process for its production.

Binding ionizable substances to ion exchange resins is not new. It is mentioned in the standard works of pharmaceutical technology as one possibility of obtaining oral administration forms exhibiting a prolonged release. U.S. Pat. No. 2,990,332 describes such an oral system having a prolonged release period. However, the active substance release in such a simple ion-exchange-resin-active-substance complex takes place over an only relatively short period, and not over a minimum time of about 4 hours required for a controlled-release preparation.

Improvements are described in U.S. Pat. Nos. 3,138,525; 3,499,960 and 3,594,470; Belgian Patent No. 729,827, and German Patent No. 2,246,037. According to these patents, the ion exchanger particles may be provided with an additional coating for controlling the active substance release in order to achieve a prolonged release period. U.S. Pat. No. 4,221,778 proposes to impregnate the ion exchanger particles, after having been charged with active substance and prior to coating with the control membrane, with an agent which prevents excessive swelling of the ion exchanger particles on their contact with water or gastrointestinal juice, and thus prevents a decomposition of the control membrane that would result therefrom.

Another application of ion exchangers is to bind pharmaceutical active substances in order to improve their unpleasant taste (DE-OS 3028082) and their unpleasant odor (CH-PS-3 83 552), respectively.

Uncharged basic ion exchangers have been used as drugs to reduce the blood cholesterol level for a long time. Their action is based on the fact that they bind bile acids in the intestinal tract and cause their excretion. The resorption prevented thereby results in an interruption of the so-called enterohepatic circulation. The organism reacts with an increased transformation of cholesterol into bile acid, directly resulting in a reduction of the blood cholesterol level.

The object of the present invention is to provide an oral administration form having acid active substances and a process for its production. This oral administration form has a high exchange capacity of an ion exchange carrier, allowing the transformation of liquid and low-melting active substances into a free-flowing, temperature-insensitive granulate, without having to use additional solvents. In case of active substances which are slightly soluble in the acid gastric juice, higher concentrations of dissolved active substance may be obtained by this granulate and a rapid or retarded release of the active substance from the administration form may be achieved by means of selective measures.

Most surprisingly, it was found that one ion exchanger used in medicine for a long time, colestipol or colestipol hydrochloride, is excellently suitable as a carrier for acidic active substances and combines the following advantages for the administration form:

a. high exchange capacity, b. liquid active substances may be transformed into a free-flowing granulate without any additional auxiliary agents and solvents, c. low-melting active substances may be transformed from the melt into a practically temperature-insensitive granular powder without having to use additional solvents, d. good flow behavior of the granulate both in uncharged and charged condition, e. the release from the active substance/carrier complex takes place very rapidly and meets, or even exceeds the requirements with respect to a rapidly disintegrating administration form, f. higher concentrations of dissolved active substance possibly appear in case of active substances which are slightly soluble in the acid gastric juice, g. a prolonged release may be achieved by additional measures, h. owing to many years of experience, established toxicological safety at a high dosage to treat pathologically high cholesterol levels.

Chemically, colestipol hydrochloride is a cross-linked polymer of diethylenetriamine and 1-chloro-2,3-epoxypropane wherein every 5th nitrogen atom is present in protonated form caused by synthesis.

If necessary, colestipol hydrochloride may also completely be transformed into the free base without any difficulties by a treatment with aqueous bases in order to use it according to the present invention.

The therapeutic colestipol hydrochloride dose for a reduction of the blood cholesterol level amounts to up to 30 g per day. Minimum side effects are to be observed; and for this reason it is safe to assume that it may be considered as free from any side effects if taken in amounts of up to one gram per day. At this dosage, the influence on a blood lipid level which is within the limits of normal can be neglected.

The exchange capacity of colestipol hydrochloride was determined to 8.1 milliequivalents by means of back titration with a NaOH-solution after reaction with a hydrochloric-acid solution of exactly known concentration. As compared to other, more technical ion exchangers this is a quite high value and corresponds, for example, to 1.6 g ibuprofen. Ibuprofen is a frequently used analgesic available over the counter at 200 mg per single dose. Thus, the complex colestipol/ibuprofen corresponding to this single dose has a total weight of only 325 mg at a maximum charge. This amount can therefore be filled into a commercial capsule (e.g., a hard gelatin capsule) without any difficulties.

Owing to its tertiary amino groups colestipol hydrochloride belongs to the weak anion exchangers.

If charged with acids, a. the basic nitrogen atoms are transformed by protonation into the corresponding ammonium salt and b. the chlorine ions of the nitrogen atoms which are present as hydrochloride are replaced by the new acid anion.

Since most of the nitrogen atoms in colestipol hydrochloride are present in the non-protonated state, colestipol must be reacted with the free active substance acid for charging purposes. Normally, ion exchangers are charged by contacting them with a solution of the substances with which the respective exchanger is to be charged. Since the non-protonated nitrogen atoms are weak bases and the active substances in general are only weak acids, the equilibrium of this reaction, owing to chemico-physical laws, is on the side of the reactants. In this special case, colestipol can therefore only be charged with active substance up to a small fraction of its maximum exchange capacity.

Most surprisingly, it was also found that liquid active substance acids or those melting in the undecomposed state can be bound to colestipol from the liquid phase within about 15 minutes, without having to use solvents. Under these conditions charging up to the theoretical charge limit is easily possible. This process may be carried out with any active substance which melts in undecomposed state below the decomposition temperature of colestipol at about 180° C. The reaction product is a free-flowing granulate, as is colestipol itself. The charge can only be seen under the microscope, making visible an increase in size of the individual, nearly spherical granular particles. In case of active substances which cannot be converted into their melt owing to their thermolability, there is the possibility of mixing them with auxiliary agents suitable for melting-point depression. As a matter of fact, this possibly non-absorbable inactive ingredient must not impair the release behavior and other important properties of the administration form.

Whereas the uncharged colestipol can practically not be ground by means of ball mills and similar methods, this can easily be done with the charged colestipol. The reason is an extremely increased internal strain which is also responsible for the increase in particle size and which is caused by the charging.

For the production of the finished administration form, the charged colestipol may simply be filled into a usual hard gelatin capsule in unground state, or it may be further processed into any other known solid administration form after grinding, for example into tablets. Alternatively, the colestipol may also be ground in moist condition —water also results in a strong swelling—and charged with active substance only after drying.

The bond to colestipol is an excellent possibility of transforming suitable active substances which are liquid or low-melting at room temperature—representing problematic active substances from the galenic point of view—into a solid, temperature-insensitive form which can easily be processed further.

Acid active substances are slightly soluble in the likewise acid gastric juice. This is a considerable disadvantage when a rapid onset of action is desired. It turned out in corresponding tests that the active substance forms a supersaturated solution in the gastric juice, and that possibly even active substances which are present in crystalline form at the body temperature of 37° C. are released in liquid form.

Owing to the increased thermodynamic activity of active substances which are liquid below their melting point, this results also in an increased proportion of dissolved active substance, thus allowing an accelerated absorption connected with an earlier onset of action.

This will be exemplified with S (+)-ibuprofen. Whereas the racemic ibuprofen has a melting point of 77°–78° C., the solely effective S (+)-enantiomer already melts at 52°–53° C. Owing to this low melting point and to some other unfavorable physical properties, this substance is a very problematic one with respect to conventional tableting, as regards handling. The resulting tablets, as any other solid administration form comprising the free active substance acid, have the disadvantage that even a short exposure to temperatures above the melting point of S (+)-ibuprofen irreversibly damages the administration form with respect to its physical properties and in particular to its active substance release.

Figure 1B:
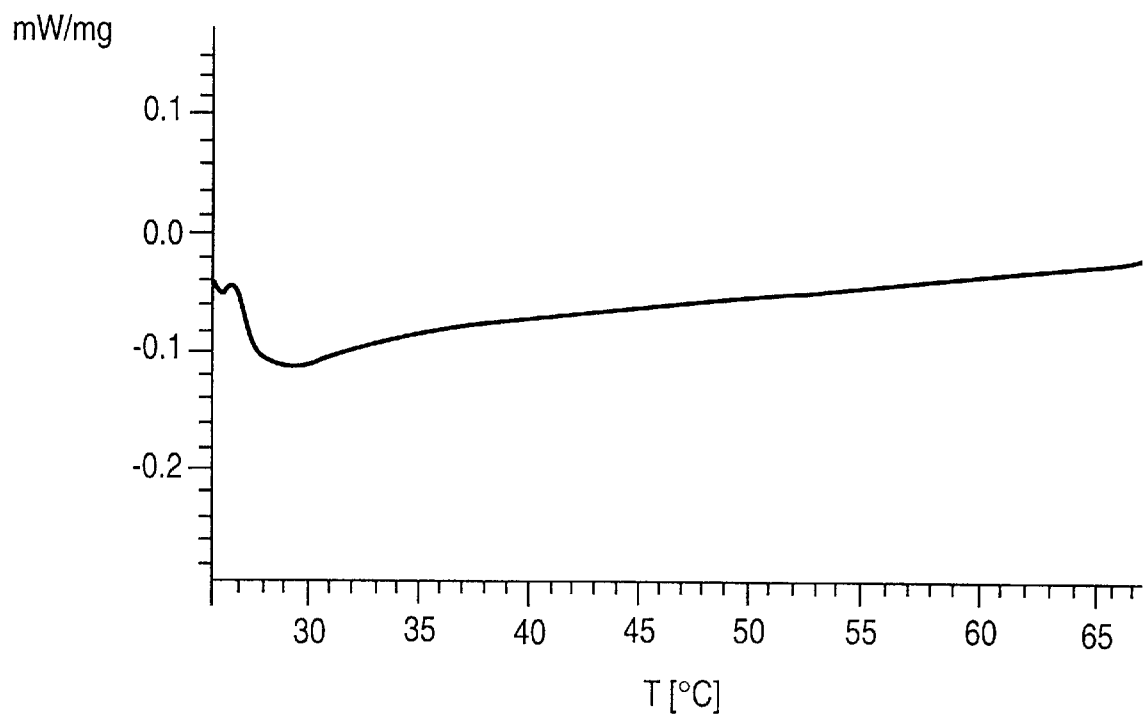

After having been bound to colestipol, meltable ibuprofen can no longer be detected by means of corresponding DSC (differential scanning calorimetry) tests (FIG. 1a and 1b). Even after several years of storage, no free and consequently meltable ibuprofen can be detected by means of this analysis method. This shows that the complex has a sufficient stability for the use as a drug.

Figure 2:
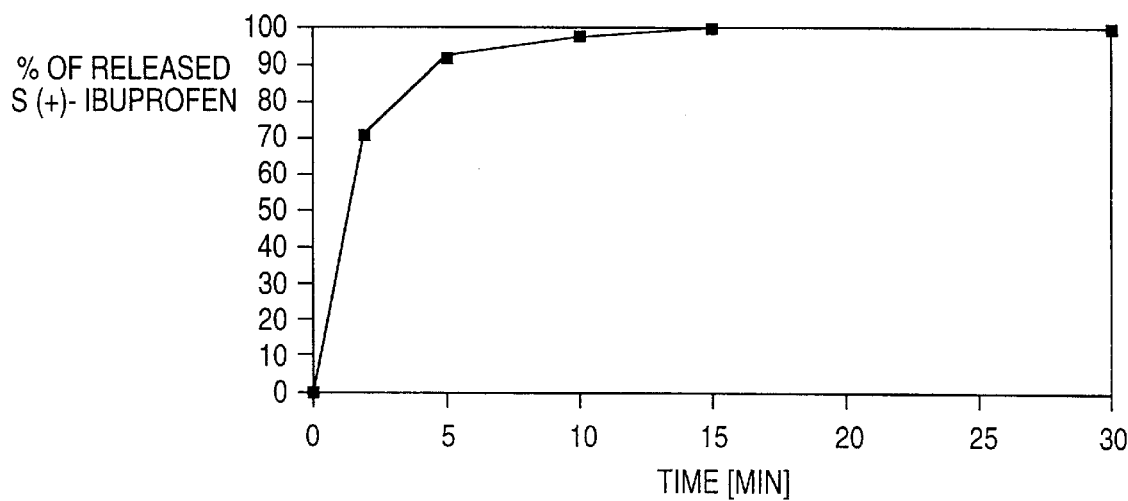

FIG. 2 shows the release of 200 mg S (+)-ibuprofen bound to colestipol in 900 ml of a phosphate buffer with a pH of 6.8. This test was carried out in a Dissolution Tester according to the Paddle Method at a temperature of 37° C. It showed that more than 80% of the active substance contained in the capsule were released after only 5 minutes.

Thus all requirements made for rapidly releasing drugs are met with respect to the release rate.

In order to determine the saturation solubility of free S (+)-ibuprofen and of S (+)-ibuprofen bound to colestipol both forms were added in sufficient excess to 100 ml of artificial gastric juice, and the concentration of dissolved S (+)-ibuprofen was measured after establishment of the equilibrium. It turned out that 4.5 ml/100 ml dissolved when free S (+)-ibuprofen was used, with a value of 13.8 g/100 ml when the colestipol complex was used. This is an increase in the solubility by factor 3.

Since it may be assumed that the saturation solubility will be achieved when S (+)-ibuprofen powder is used, the normal saturation solubility must be exceeded when the ibuprofen/colestipol-complex is used. When the release is observed under the microscope (FIG. 3; 1 colestipol particles, 2 liquid S (+)-ibuprofen, 3 recrystallized S (+)-ibuprofen; magnification 200×), it is seen that the active substance is released in liquid form and that it recrystallizes only sporadically and spontaneously from this liquid phase. Since the liquid phase of the S (+)-ibuprofen, which actually is solid at 37° C., represents a state of increased thermodynamic activity, this automatically explains the higher solubility in artificial gastric juice.

This increased solubility in gastric juice and the kinetically uninhibited release of the ibuprofen from the complex make it possible that the active substance is released already in the stomach more rapidly, as compared to conventional ibuprofen preparations. This is an invaluable advantage for an analgesic which is in most cases taken in acute pain, such as head and tooth ache.

In case a rapid active substance release is not desired, controlled-release preparations may also be manufactured with the colestipol/active substance complexes. In case of low-melting active substances, the advantage of temperature-insensitivity still remains.

For the manufacture of such sustained-release drugs any conventional retardation method known to those skilled in the art may be applied in principle. It may possibly be advantageous to use the complex in ground condition. This is particularly true when compressed articles in the form of tablets are to be manufactured by using suitable auxiliary agents known to the skilled artisan.

In case of S (+)-ibuprofen it has proved to be particularly advantageous to granulate unground charged colestipol with Na-alginate and then to fill it in capsules dissolving in gastric juice. The gel film of the granular powder forming on contact with gastric juice forms a diffusion barrier and thus causes a slow release of the ibuprofen over a period of up to 8 hours.

Figure 4:
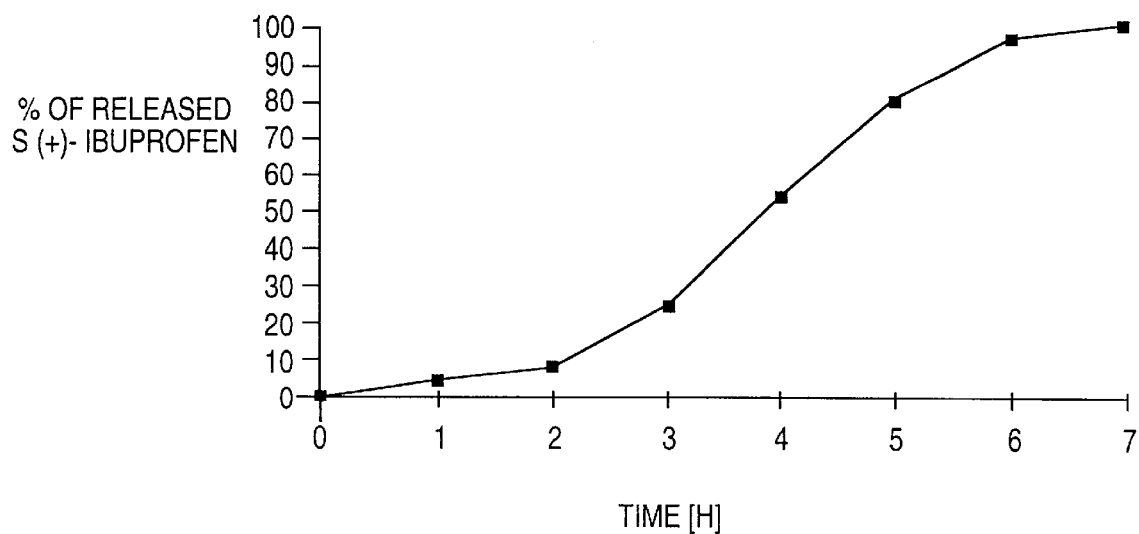

FIG. 4 shows the result of a release experiment according to the so-called Half-Change-Method. According to this method, the passage of an administration form through the gastrointestinal tract is simulated by means of gradually increasing the pH-value. To this end, each time the samples are taken half of the release medium initially consisting of artificial gastric juice is replaced by artificial intestinal juice.

The course of the graph shows that the whole ibuprofen contained in the administration form is continuously released over a period of about 8 hours.

The results shown by the example of S (+)-ibuprofen can be transferred to other active substances. This particularly applies to active substances belonging to the group of nonsteroidal anti-rheumatics, such as indometacin, acemetacine, sulindac, tolmetin, diclofenac, lonazolac, ketoprofen, ibuprofen rac., flurbiprofen, fenoprofen, naproxen, pirprofen, indoprofen, caprofen, and tiaprofenic acid, but also to substances, such as valproic acid, an antiepileptic, and captopril, an antihypertensive.

To sum it up the Figures show:

FIG. 1a
DSC-examination of S (+)-ibuprofen
heating rate: 10K/min.
Gas atmosphere: air FIG. 1b
DSC-examination of S (+)-ibuprofen/colestipol-complex
Heating rate: 10K/min.
Gas atmosphere: air FIG. 2
Release rate of S (+)-ibuprofen bound to colestipol from hard gelatin capsules soluble in gastric juice.

Figure 3:
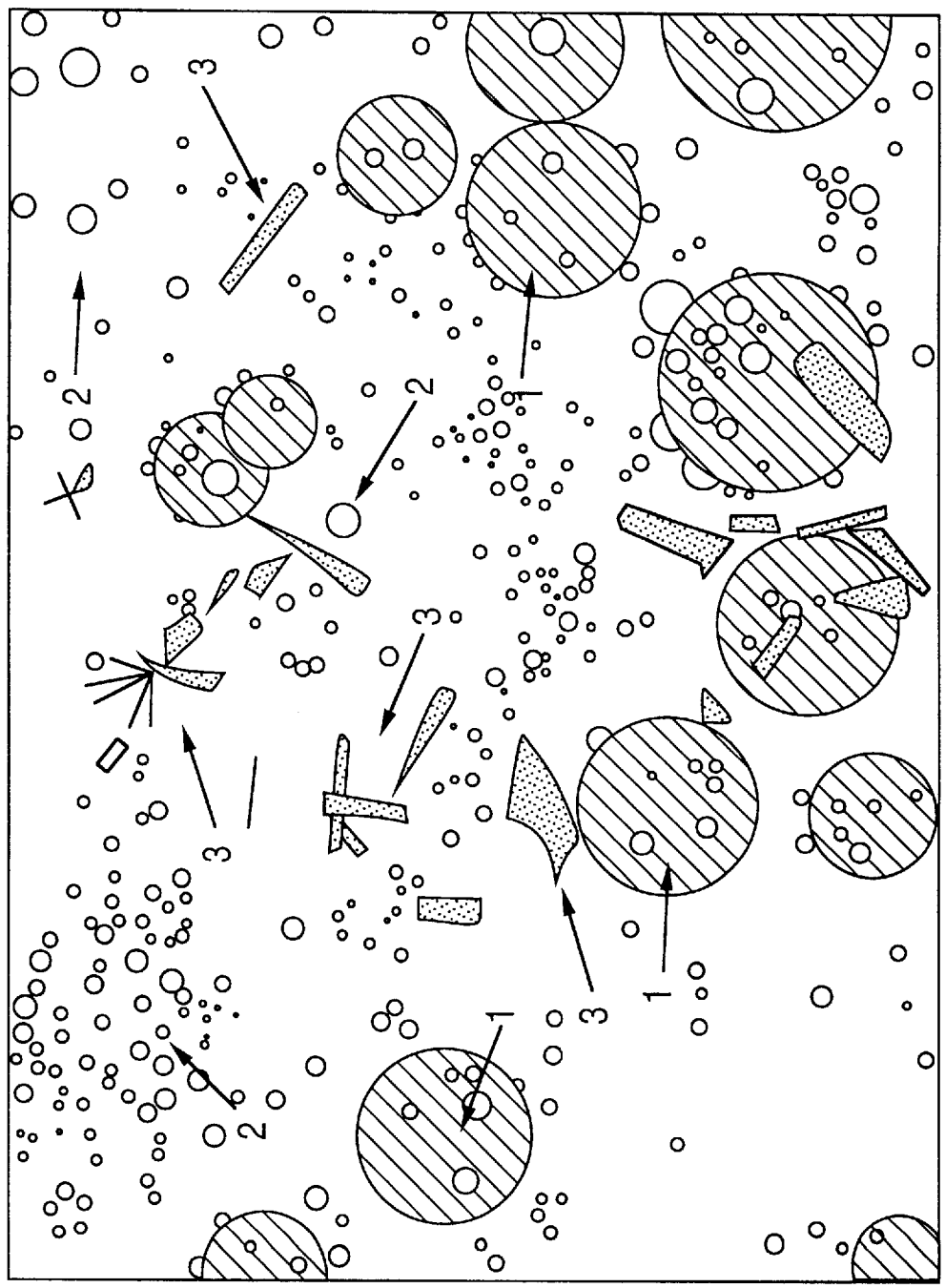

FIG. 3
S (+)-ibuprofen-complex on contact with artificial gastric juice; microscopic photograph, magnification: 200×.

FIG. 4
In-vitro release of S (+)-ibuprofen according to the Half-Change method (n=6; vertical beams represent the standard deviation).

EXAMPLES

1. Rapidly releasing S (+)-ibuprofen formulation 72 g of S (+)-ibuprofen is melted and heated to 80° C. Under stirring, 48 g of colestipol hydrochloride is added, and this mixture is kept at 80° C. for 25 minutes under continued stirring or mixing. Subsequently, a "dry" granulate has formed, and, after cooling to room temperature, 333 mg (200 mg active substance) thereof is each dosed into gelatin capsules soluble in gastric juice.

2. Slowly releasing S (+)-ibuprofen formulation 27.5 g Na-alginate is added to 110 g of the granulate of Example 1 charged with S (+)-ibuprofen and mixed carefully. Then, 138 g of deionized water is added, and the forming pasty mass is homogenized by kneading. A granulate strand (diameter: 0.7 mm, length: 1 mm) is manufactured from the doughy mass, and the dry granular powder is filled in doses of 432 mg each (corresponding to 200 mg of active substance) into gelatin capsules which are soluble in gastric juice.

3. Rapidly releasing captopril formulation 64 g of captopril is molten and heated to 100°–110° C.

Under stirring, 48 g of colestipol hydrochloride is added. This mixture is kept at 100°–110° C. for 25 minutes under continued stirring or mixing. Afterwards, a "dry" granular powder has formed, and, after cooling to room temperature, 43 mg (25 mg active substance) is each dosed into gelatin capsules soluble in gastric juice.

We claim:

1. In a pharmaceutical preparation in oral administration form having a carrier for an acidic active substance wherein the active substance has at least one free carboxyl group ionically bound to a polymer having tertiary amino groups, the improvement wherein the polymer is colestipol or colestipol hydrochloride, and is present in an amount which is less than the pharmaceutically active amount thereof, utilizing acid addition to the non-protonated nitrogen of colestipol pharmaceutical preparation being obtained by binding an acidic active substance from a liquid solvent free phase to the basic groups of colestipol or colestipol hydrochloride.

2. A pharmaceutical preparation according to claim 1 wherein the active substance is a nonsteroidal antirheumatic.

3. A pharmaceutical preparation according to claim 2 wherein the active substance is a derivative of anthranilic acid, acetic acid, or propionic acid.

4. A pharmaceutical preparation according to claim 1 wherein the active substance is in the form of a racemate.

5. A pharmaceutical preparation according to claim 1 wherein the active substance has at least one chiral center and is present in a substantially pure enantiomeric form.

6. A pharmaceutical preparation according to claim 3 wherein the active substance is ibuprofen.

7. A pharmaceutical preparation according to claim 6 wherein the active substance is S (+)-ibuprofen.

8. A pharmaceutical preparation according to claim 1 wherein the active substance is valproic acid.

9. A pharmaceutical preparation according to claim 1 wherein the active substance is captopril.

10. A pharmaceutical preparation according to claim 1 in the form of a chewable tablet or a chewing gum.

11. A pharmaceutical preparation according to claim 1 in the form of a capsule or a tablet.

12. A process for the production of a pharmaceutical preparation according to claim 1 which comprises binding an acidic active substance from a liquid solvent-free phase to the basic groups of colestipol or colestipol hydrochloride.

13. A process for the production of a pharmaceutical preparation according to claim 1 which comprises mixing an acidic active substance with an auxiliary agent or melting-point depression agent, and binding the acidic active substance from a liquid solvent-free phase to the basic groups of colestipol or colestipol hydrochloride from said mixture.

* * * * *